US010195775B2

(12) United States Patent
Burz et al.

(10) Patent No.: US 10,195,775 B2
(45) Date of Patent: Feb. 5, 2019

(54) CUSHION, METHOD OF AND APPARATUS FOR MOLDING A CUSHION FOR A RESPIRATORY MASK (75) Inventors: Johann S. Burz, Germaringen (DE); Achim Biener, Aufkirchen (DE); Johannes Nickol, München (DE); Bernd Lang, Gräfelfing (DE)

(73) Assignee: ResMed R&D Germany GmbH, Martinsried (DE)

( * ) Notice: Subject to any disclaimer, the term of this patent is extended or adjusted under 35 U.S.C. 154(b) by 1697 days.

(21) Appl. No.: 12/737,538

(22) PCT Filed: Jul. 22, 2009

(86) PCT No.: PCT/EP2009/005325
§ 371 (c)(1),
(2), (4) Date: Apr. 11, 2011

(87) PCT Pub. No.: WO2010/009877
PCT Pub. Date: Jan. 28, 2010

(65) Prior Publication Data
US 2011/0174310 A1 Jul. 21, 2011

(30) Foreign Application Priority Data
Jul. 22, 2008 (EP) .................................. 08160921

(51) Int. Cl.
A61M 16/06 (2006.01)
B29C 45/44 (2006.01)
B29K 83/00 (2006.01)

(52) U.S. Cl.
CPC ......... B29C 45/4407 (2013.01); A61M 16/06 (2013.01); A61M 16/0616 (2014.02);
(Continued)

(58) Field of Classification Search
CPC ....... A61M 16/06; A61M 2016/06–2016/0661
(Continued)

(56) References Cited

U.S. PATENT DOCUMENTS 1,625,644 A * 4/1927 Fisher ........................... 152/327
2,185,568 A * 1/1940 Ratner ........................ 264/46.9
(Continued)

FOREIGN PATENT DOCUMENTS

DE 10 2005 033 649 1/2007
DE 10 2005 033 650 1/2007
(Continued)

OTHER PUBLICATIONS

International Search Report for PCT/EP2009/005325, dated Jan. 5, 2010.
(Continued)

Primary Examiner — LaToya M Louis
(74) Attorney, Agent, or Firm — Nixon & Vanderhye P.C.

(57) ABSTRACT

The present invention is related to a cushion (1) for a respiratory mask, to a method of manufacturing such a cushion (1) as well as to a respiratory mask including a cushion (1) and an apparatus for manufacturing a cushion (1) for a respiratory mask. It is particularly referred to a method of manufacturing a cushion (1) for a respiratory mask, comprising the steps of providing a mold comprising at least two mold halves (11, 13) and at least one core (12) therein, closing the mold, injecting a first material into the mold to form the cushion (1), wherein the core (12) is enclosed by the cushion (1) thereby forming at least one cavity (4), opening the mold, removing the core (12) from the cushion (1) to provide the at least one cavity within the cushion (1), and sealing the cavity (4).

41 Claims, 9 Drawing Sheets (52) U.S. Cl.
CPC ..... *A61M 16/0622* (2014.02); *A61M 2207/00* (2013.01); *B29K 2083/005* (2013.01)

(58) Field of Classification Search
USPC .... 128/898, 205.25, 206.21, 206.24, 206.28, 128/207.13; 264/250, 328.1, 328.3
See application file for complete search history.

(56) References Cited

U.S. PATENT DOCUMENTS

| | | | | |
|---|---|---|---|---|
| 2,296,105 | A * | 9/1942 | Hansen | 264/163 |
| 7,827,990 | B1 * | 11/2010 | Melidis et al. | 128/206.24 |
| 2001/0025641 | A1 * | 10/2001 | Doane et al. | 128/207.15 |
| 2004/0149287 | A1 * | 8/2004 | Namey, Jr. | 128/205.25 |
| 2005/0199239 | A1 * | 9/2005 | Lang et al. | 128/206.24 |
| 2009/0078267 | A1 * | 3/2009 | Burz et al. | 128/206.24 |
| 2010/0170516 | A1 * | 7/2010 | Grane | 128/206.26 |

FOREIGN PATENT DOCUMENTS

| | | |
|---|---|---|
| EP | 0 602 424 | 6/1994 |
| GB | 2 367 525 | 4/2002 |
| JP | 5-24055 | 2/1993 |
| WO | WO 2007009782 A1 * | 1/2007 |
| WO | WO 2009/062265 | 5/2009 |
| WO | WO 2009/143586 | 12/2009 |

OTHER PUBLICATIONS

International Preliminary Report on Patentability for PCT/EP2009/005325, dated May 25, 2010.

* cited by examiner

CUSHION, METHOD OF AND APPARATUS FOR MOLDING A CUSHION FOR A RESPIRATORY MASK

This application is the U.S. national phase of International Application No. PCT/EP2009/005325, filed 22 Jul. 2009, which designated the U.S. and claims priority to EP Application No. 08160921.6, filed 22 Jul. 2008, the entire contents of each of which are hereby incorporated by reference.

The present invention is related to a cushion for a respiratory mask, to a method of manufacturing such a cushion as well as to a respiratory mask including a cushion and an apparatus for manufacturing a cushion for a respiratory mask.

Respiratory masks are widely used in the medical and therapeutical sectors. One important employment of respiratory or breathing masks relates to treatment of sleep-related respiratory disorders, in particular of obstructive sleep apnea (OSA). Patients suffering from OSA are often supplied with breathable gas at a continuous positive airway pressure during rest or sleep periods. This is achieved by the patient wearing a suitable breathing mask which is connected to a breathing apparatus providing breathable gas at the necessary pressure. Due to the pressure being higher than ambient pressure the obstructed airways of the patient are pushed open, also referred to as "pneumatic splinting", allowing for an adequate supply of breathable gas, such as air or oxygen. Respiratory masks, also referred to as patient interface, usually cover mouth and/or nose of a patient or user.

Since this treatment often has to continue throughout the entire rest or sleep phase, the mask has to be as comforting to the patient or user as possible and to be adapted for long-time use. Respiratory masks therefore often comprise a cushion, e.g. a gel cushion, whose purpose it is to provide a soft and comforting contact zone or interface between the skin of the patient's face and the mask. Such cushions also establish a seal between the mask and the patient's skin so that the mask interior is sealed from ambience. This is of relevance particularly in the field of, e.g., CPAP or BiPAP, breathing therapy where breathable gas is supplied at elevated pressures. The provision of a tight seal and avoidance of leaks is important to achieve a reliable and predictable breathing pressure and thus an effective therapy. These cushions need to be soft and cushy on the one hand, yet have to provide enough stability and rigidity on the other hand to keep the mask in place and to establish the required seal.

It is known to manufacture a two-component cushion comprising an outer shell of a first and an interior of a second material, such as a gel. However, manufacturing of those cushions is often rather complex, time consuming and thus costly process. In addition, it is generally required to provide a biocompatible, easy to clean and hygienic patient interface and cushion.

There is thus a need for an improved cushion for a respiratory mask, for an improved patient interface including a cushion, for an improved method of manufacturing such a cushion, and for an improved apparatus for manufacturing a cushion for a respiratory mask.

It is an object of the present invention to provide an improved cushion for a respiratory mask, an improved mask including a cushion, and/or an improved method and apparatus for manufacturing such mask or cushion, which preferably overcome the deficiencies of the prior art. It is, in particular, an object that said cushion has improved characteristics and/or is more easily and cost-efficient to manufacture. It is another object of the present invention to provide an improved method of and an improved apparatus for producing a cushion for a respiratory mask. According to a further object said method shall be more simple and efficient.

These objects are achieved by the features of the independent claims. The dependent claims relate to preferred embodiments.

The present invention is, i.a., directed to a method of manufacturing a cushion for a respiratory mask. The method comprises the steps of providing a mold comprising at least two mold halves and a core therein, closing the mold, injecting a first material into the mold to form the cushion, wherein the core is enclosed by the cushion, opening the mold, removing the core from the cushion to provide a cavity within the cushion, and sealing the cavity. According to a preferred embodiment, the cavity is filled with a filler medium before sealing.

According to a preferred embodiment the mold comprises only one core, and preferably only one core per cavity. It is furthermore preferred that the core consists of a single part. Thus, when the core is ejected or demolded from the cushion only one opening or orifice, preferably per cavity, remains within the cushion. According to a preferred embodiment the mold comprises two or more cores, each for providing a distinct cavity. Thus, preferably two cores, which are e.g. bent, are provided to establish two cavities, i.e. one cavity each. The two cores preferably provide one cavity at each side of the cushion. In this case the cushion preferably has two orifices, preferably at opposite sides of the cushion.

Preferably, the core is generally C-shaped or V-shaped with a rounded tip. However, other shapes do also fall within the scope of the present invention. For instance, the core can be semicircular, bar-shaped with bent ends or the like. The skilled person will understand that the core has to be shaped in such a manner as to allow for a demolding from the cushion. Preferably the shape of the core is chosen such that the step of removing the core from the cushion leaves a single orifice in the cushion. Alternatively or additionally, the shape of the core is chosen in such that the cavity provided in the cushion has an advantageous shape and/or structure leading to an improved cushion. The core does preferably not exhibit a ring-structure and thus is not a closed structure. Preferably, the opening or orifice is smaller than the extensions of the core wherein demolding is possible due to elastic or elongation properties of the molded cushion. These properties preferably allow the orifice to be temporarily enlarged for demolding wherein the cushion subsequently returns to its molded shape. Preferred materials will be discussed further below. This structure and procedure allows the provision of a large cavity in the molded cushion while only a comparatively small hole or orifice is to be provided in the cushion, particularly suitable for subsequent easy and advantageous filling and sealing. Preferably, the preferably C-shaped core is of large dimensions while the hole is of small, preferably substantially rectangular, dimensions. As will be discussed further below, the relevant and comparable dimensions (width, length) of the orifice are in the range of about 1/1.5 to 1/8 and preferably between about 1/2 to 1/6 of the core's respective largest dimension (largest width, largest height).

The cushion to be manufactured comprises a support plane, i.e. the plane which is supported on the patient's face once the patient is wearing the respiratory mask. It is preferred that the core is arranged in such a manner in the mold, that the cavity formed by said core extends essentially in a plane parallel to this support plane. In other words, the contour of the preferred "C" or "V" proceeds through or in a plane, which is substantially parallel to the support plane.

According to a preferred embodiment, the core is made of tool steel, in particular of sintered tool steel, or aluminium. The core comprising or being made of aluminium sintered material, such as sintered steel allows the provision of advantageous shapes of the core. Moreover, sintering allows easy provision of channels inside the core, e.g., for conducting compressed air for demolding. This particularly speeds up the production cycle.

The core can be an integrated part of one of the mold halves. It is preferred that the core is moveable with respect to one or both of the mold halves. Preferably, the core is movably connected to one of the mold halves.

It is preferred that the step of removing the core from the cushion comprises opening the mold, displacing the core together with the cushion relative to the mold halve(s). Thus, the molded cushion is first removed from the mold halves and afterwards detached from the core. This enables a more easy demolding step. The core can be removed from the cushion by either detaching the cushion from the core or demolding the core from the cushion. This can preferably be done automatically, e.g. by means of a robot, which is adapted to capture or grip a part or portion of the cushion in order to detach the cushion from the core or to demold the core from the cushion.

In addition or alternatively, detaching the cushion is preferably performed by air pressure. In one embodiment, the air pressure is provided through the core, e.g. through air canals or conduits in the core. Thus, the cavity formed within the cushion is inflated to a certain degree which facilitates detaching the cushion from the mold.

Once the cushion is demolded, the cavity is sealed. Preferably, sealing is performed by injecting the first material into the orifice(s)/opening(s) left behind by the removed core. It is also preferred to seal the cavity with a material different from the first material, preferably a material being of the same kind but a different grade, e.g., hardness, than the first material. One preferred example for a material suitable for sealing the cavity is a silicone having a Shore A hardness in the range of about 5 to 20, preferably of about 10. Alternatively, the cavity is sealed by gluing an insert into the orifice. In any case, the step of sealing the cavity closes the cavity, preferably airtight, against the environment.

Alternatively or additionally, after the first injection molding step forming the cushion, one of the mold parts is opened and the core is demolded from the cavity while the cushion remains seated in the remaining mold part. After demolding of the core, the cavity is filled. The mold is subsequently closed and the cavity is sealed by a second injection molding step.

According to a preferred embodiment, the first material is or comprises one or more of a flexible first material, e.g., a plastic or synthetic material such as an elastomer material or a material comprising elastomer components. For example, the cushion may be made of silicone such as liquid silicone rubber (LSR), or thermoplastic elastomer (TPE). In an embodiment, an open hollow structure may be an injection molded skin, e.g., made of silicone, a liquid silicone rubber (LSR), plastic, or TPE.

It is preferred that the method further comprises the step of filling the cavity with a second material prior to sealing the cavity. Preferred examples for the second material include a fluid, i.e., a gaseous, dispersible and/or liquid fluid, an expandable fluid, a foam, a powder, beads and/or gel. According to embodiments, a mixture of the above media may be used, e.g., two gels of different hardness or viscosity.

Such second material is preferably silicone, silicone gel, silicone foam, PU gel, PU foam, oil, and/or air. It is particularly preferred that the second material has a lower Shore-hardness than the first material.

Preferably, the shore hardness of the cushion element is in the range of about 10 to 20 Shore 000. Preferably, the second material, e.g. a gel, preferably silicone gel, has a Shore 000 hardness in the range of about 10 to 20, preferably between 11 and 19, and more preferably between 12 and 18, between 13 and 17, between 14 and 16, and also preferable of about 15. The first material preferably has a Shore A hardness in the range of about 20 to 60, preferably in the range of about 35 to 45.

According to a further preferred embodiment, the cushioning element has a Shore 000 hardness in the range of about 45 to 90. The second material, e.g. a gel, preferably silicone gel, preferably has a Shore 000 hardness in the range of about 45 to 90, preferably between about 50 and 90, and more preferably between about 50 and 80, between about 60 and 75, between about 50 and 70, and also preferable of between about 50 and 70. The first material preferably has a Shore A hardness in the range of 20 to 60, preferably in the range of about 35 to 45. Preferably, filler materials as described in WO 2009/062265, filed 17 Nov. 2008, and PCT/AU2009/000682, filed 29 May 2009, are used, which are herewith incorporated by reference.

Further preferably, the cavity is sealed by using a third material, preferably a material discussed above with regard to the first and/or second material. Such a third material may be provided in the form of a plastic clip or other functional means. Also preferably, the seal of the cavity or orifice is formed as a fastening or securing means for allowing fixation of the cushion to a patient interface, e.g. a mask frame. Sealing may be preferably achieved by means of a two component injection molding step, where a first, preferably soft, material and a second, preferably harder material are jointly or subsequently molded to the cushion for sealing the cavity. In such embodiment, the softer material advantageously provides the seal, preferably being suitable for compensation of shrinkage of the filler medium, whereas the harder material is suitable for fulfilling some function, e.g., as a securing means. The sealing materials can also suitably provide haptic information, e.g., for proper positioning or alignment of the cushion vis-à-vis a patient interface to which it is to be connected. Preferably, the seal is a dosage unit for dosing the proper amount of filler medium and/or adhesive and remains adhered to the cushion thereby sealing the orifice after filling of the adhesive and/or filler medium. Preferably, the second forms, is in the form of or applies, simultaneously with sealing of the orifice, a functional means, such as a fastening means, a handling means, particularly for handling during production, or the like. Such means preferably has a predetermined breaking point in order to allow removal and disposal prior to packaging.

According to a preferred embodiment, the rigidity and/or resiliency of the cushion can be adjusted by varying the thickness of the cushion walls. Therein, varying the thickness of the cushion walls is preferably achieved by varying the thickness of the core. Additionally or alternatively, the geometry, such as size and thickness, of the core can be varied in order to influence the wall thickness and the like of the cavity, either along the cross section of the cavity and/or along the circumference of the cavity or the cushion. For example, the outer wall may be thin in specific areas whereas the inner wall is thicker. In particular, the inner, outer, upper and lower walls of the cavity can be influenced independently of one another. Alternatively or additionally, the rigidity of the cushion can be adjusted by providing ribs and/or grooves within the inner surface of the cushion's walls defining the cavity. Therein, providing ribs and/or grooves is preferably achieved by providing grooves and/or ribs on the surface of the core. This particularly allows the provision of structures influencing the rigidity and/or resiliency of the cushion while maintaining its outer structure, e.g., smooth and homogenous. The structures are formed inside the cushion, in the cavity achieved by the core.

According to a preferred embodiment, the core is shaped to allow the provision of longitudinal and/or transverse walls in the cavity (i.e., longitudinal with regard to the elongate extension of the cavity along the cushions circumference and/or transverse thereto), which result in the provision of multiple chambers and distinct areas in the cavity. Such chambers or areas are preferably filled with different (second) filler materials having differing characteristics. Thereby the rigidity and/or resiliency of the cushion can be advantageously influenced and adapted. In particular, the rigidity and resiliency is aligned with the sealing and comfort requirements of different regions of a wearer's or user's skin/face on which cushion is to be placed. If multiple cavities are achieved by using two or more cores, each of the cavities is preferably filled with an individual filler medium, preferably with different materials having different properties.

The above measures particularly allow adjustment of the flexibility, hardness and/or elasticity of the cushion, in each cross section and/or along at least parts of its circumference, to the patient's needs.

According to a further preferred embodiment, the core is provided with recessed and/or protruding marks, e.g., a sign, a logo, letters, or other information, which are molded into the walls of the cavity during molding of the cushion. Preferably, the marks are provided on the core in such a manner that, after molding of the cushion, the sign, the letters etc. are clearly visible and legible from the outside. This allows an easy and reliable way of providing signs etc. onto the cushion suitable for conveying information to the user. Such information preferably includes the manufacturers brand, the (trade)name of the cushion or patient interface, the size of the cushion or the patient interface, an indication on the orientation needed to connect the cushion with a patient interface. In the latter case the interface preferably comprises corresponding information allowing easy and fast alignment of cushion and interface for connection to one another. The provision of the sign, letters or other information inside the cavity via the core during molding is of particular advantage. The application of the information is achieved easily and reliably without any additional processing steps. Furthermore, particularly since the cavity is preferably filled with a filler medium and then sealed, the information is protected against the environment and will neither be contaminated nor soiled during use.

The present invention further relates to an apparatus for manufacturing a cushion for a respiratory mask, and preferably for performing the method according to the present invention. Such apparatus preferably comprises the features of the mold, particularly discussed in relation to the method of the present invention.

The present invention further relates to a cushion for a respiratory mask. The cushion may, in particular, be manufactured according to the method and/or by the apparatus described above. The cushion according to the invention comprises a sealed hollow structure, preferably of basically ring shape and more preferred of triangular shape, adapted to fit to a patient's face and to cover a patient's mouth and/or nose. Said hollow structure is made of a first material, wherein the hollow structure comprises a cavity extending only along a part of the circumference of the, preferably triangular, structure. As discussed above, said cavity is filled with a second material, such as, e.g., a silicone gel.

Said cavity is preferably C-shaped or V-shaped with a rounded tip. However, other shapes do also fall within the scope of the present invention. For instance, the cavity can be semicircular, bar-shaped with bent ends or the like. Preferably, the cavity takes the shape(s) as referred to above when discussion the geometry of the core.

The cushion comprises a support plane, i.e. the plane which is supported on the patient's face. It is preferred that the sealed hollow structure extends essentially in a plane parallel to this support plane. In other words, the contour of the "C" or "V" proceeds through a plane, which is substantially parallel to the support plane. Thus, the filled cavity is adapted to provide sufficient stability to the structure of the cushion.

According to a preferred embodiment, the opening of the "C" or "V" is adapted for positioning at the ridge of a patient's nose. In other words the cavity does not extend to a region of the cushion which is designed to be placed over the ridge of a patient's nose. It is thus preferred, that the contour of the "C" or "V" essentially surrounds the nostrils and/or the mouth of a patient using the cushion.

As discussed above, the first material comprises preferably silicone or polysiloxane. It is further preferred that the cavity is filled with a second material. As also referred to above, preferred examples for the second material are beads, fluids, foams, gels, liquids and/or gases as well as mixtures thereof. It is particularly preferred that the second material has a lower Shore-hardness than the first material.

In the following there will be discussed further preferred embodiments of the present invention which are to be seen as both alternative and additional embodiments, referred to as aspects:

1. Method of manufacturing a cushion for a respiratory mask, comprising the steps of providing a mold comprising at least two mold halves and at least one core therein, closing the mold, injecting a first material into the mold to form the cushion, wherein the core is enclosed by the cushion thereby forming at least one cavity, opening the mold, removing the core from the cushion to provide the at least one cavity within the cushion, and sealing the cavity.
2. Method according to aspect 1, wherein the mold comprises one core per cavity to be molded, and preferably only one core.
3. Method according to aspect 1 or 2, wherein the core consists of a single part and is, preferably integrally, connected to a handling member.
4. Method according to any one of the preceding aspects, wherein the core is C-shaped.
5. Method according to any one of the preceding aspects, wherein the core is an integrated part of one of the mold halves, and preferably comprises a handling member.
6. Method according to any one of the preceding aspects, wherein the core is moveable with respect to one or both or all of the mold halves.
7. Method according to any one of the preceding aspects, wherein the core is made of steel, sintered steel, aluminium and/or sintered aluminium.
8. Method according to any one of the preceding aspects, wherein the step of removing the core from the cushion comprises displacing the core together with the cushion relative to the mold halves.

9. Method according to any one of the preceding aspects, wherein the step of removing the core from the cushion comprises detaching or demolding the cushion from the core.
10. Method according to aspect 9, wherein detaching the cushion is performed by air pressure.
11. Method according to aspect 10, wherein the air pressure is provided through the core and preferably the handling member.
12. Method according to any one of the preceding aspects, wherein the step of removing the core from the cushion leaves a single orifice in the cushion.
13. Method according to any one of the preceding aspects, wherein the cavity is sealed by injecting the first material or a similar material into or onto the orifice, and/or preferably by overmolding.
14. Method according to any one of aspects 1 to 12, wherein the cavity is sealed by gluing an insert into or a patch over the orifice.
15. Method according to any one of the preceding aspects, wherein the cavity is closed after removal of the core and subsequently the cavity is sealed by overmolding a third material, said third material preferably corresponding to the first material.
16. Method according to any one of the preceding aspects, wherein the first material comprises silicone.
17. Method according to any one of the preceding aspects, further comprising the step of filling the cavity with a second material prior to sealing the cavity.
18. Method according to any one of the preceding aspects, wherein the second material is one or a combination of: foam, gel, liquid, gas, beads, wherein these preferably comprise silicone.
19. Method according to any one of the preceding aspects, wherein the rigidity of the cushion can be adjusted by varying the thickness of the cushion wall(s).
20. Method according to any one of the preceding aspects, wherein the rigidity of the cushion can be adjusted by providing ribs and/or grooves on/within the inner surface of the cushion, i.e., the surfaces of the cushion forming the inner cavity walls.
21. Method according to any one of the preceding aspects, wherein varying the thickness and/or providing ribs and/or grooves is achieved by varying the thickness of the core and/or by providing structures such as grooves and/or ribs on the surface of the core.
22. Method according to any one of the preceding aspects, wherein there are provided two or more horizontal or longitudinal cavities which are separated by one or more horizontal walls or membranes, and/or there are provided two ore more vertical or transverse cavities or pockets which are separated by walls or membranes extending substantially vertically.
23. Method according to aspect 22, wherein there is preferably provided one core for each cavity, wherein the core preferably comprises one or more slits which allow molding of the wall(s) or membrane(s) separating different cavities or pockets.
24. Method according to any one of the preceding aspects, wherein the width and length of the orifice is about 1/1.5 to 1/8 and preferably 1/2 to 1/6 of the corresponding maximum dimension of the core, and/or wherein the size of the core and of the orifice is such that upon demolding the opening of the orifice is elongated by preferably about 50% to 700% and preferably by about 100% to 500% in width and/or length direction.
25. Cushion for a respiratory mask, in particular a cushion manufactured according to the method of any one of aspects 1 to 24, the cushion comprising a sealed hollow basically ring like structure adapted to fit to over a patient's nose and made of a first material, wherein the hollow structure comprises at least one and preferably only one cavity extending only along a part of the circumference of the cushion.
26. Cushion according to aspect 25, wherein the cavity is C-shaped.
27. Cushion according to aspect 26, wherein the opening of the "C" is adapted for positioning at the ridge of a patient's nose.
28. Cushion according to any one of aspects 25 to 27, wherein the first material comprises silicone.
29. Cushion according to any one of aspects 25 to 28, wherein the cavity is filled with one or a combination of: foam, gel, liquid, gas, and/or beads wherein each of these preferably comprises silicone.
30. Cushion according to any one of aspects 25 to 29, wherein the cushion comprises a varying rigidity due to varying the thickness of the cushion wall(s) and/or by providing ribs, grooves and/or further structures on/within the inner surface of the cushion, i.e., the surfaces of the cushion forming the inner cavity walls.
31. Cushion according to any one of aspects 25 to 30, wherein the cushion comprises two or more horizontal or longitudinal cavities which are separated by one or more horizontal walls or membranes, and/or there are provided two ore more vertical or transverse cavities or pockets which are separated by walls or membranes extending substantially vertically.
32. Cushion according to any one of aspects 25 to 31, wherein the dimension of the orifice are preferably in the range of about 20 to 50 mm in width direction and of about 3 to 10 mm in length direction, and wherein the maximum dimension of the core in width direction is in the range of about 70 to 100 mm and of about 30 to 50 mm in height direction.
33. Apparatus for manufacturing a cushion for a respiratory mask, preferably according to any one aspects 25 to 32, and preferably according to a method of any one of aspects 1 to 24, comprising at least two mold parts and a core, which is preferably C-Shaped, being connected to a handling member being moveable with respect to at least one of the mold parts.

Preferred embodiments of the present invention are described below with respect to the following figures.

FIG. 5C shows a detail of FIG. 5B.

Figure 1A:
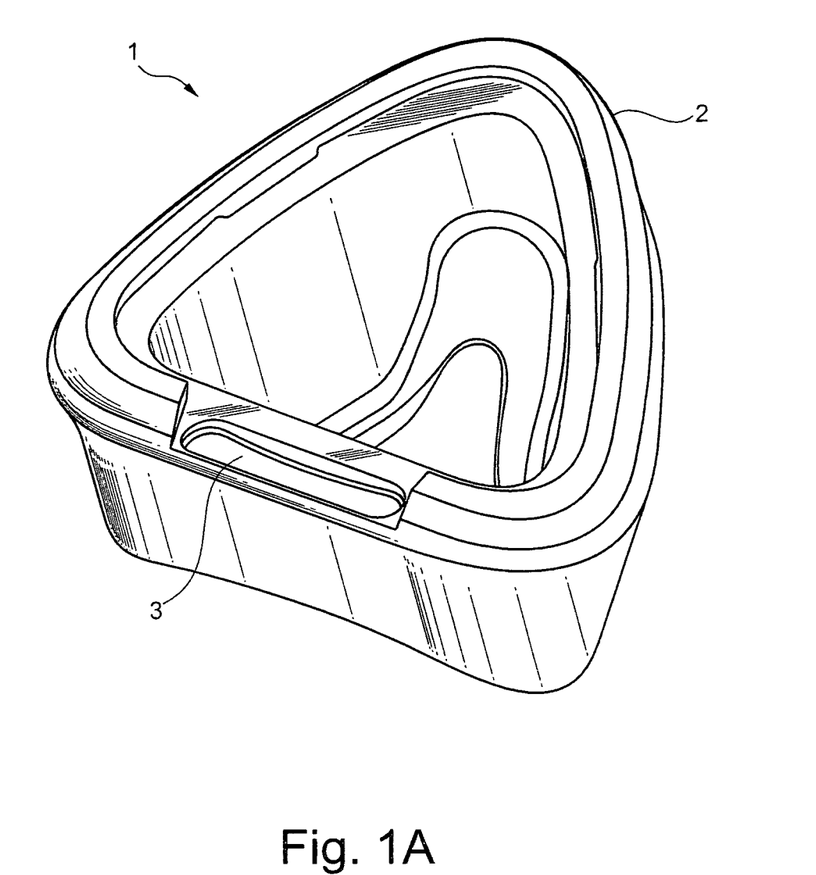
FIG. 1A (shaded) and FIG. 1B (line drawing) show a perspective view of a preferred embodiment of a cushion according to the present invention.
Figure 1B:
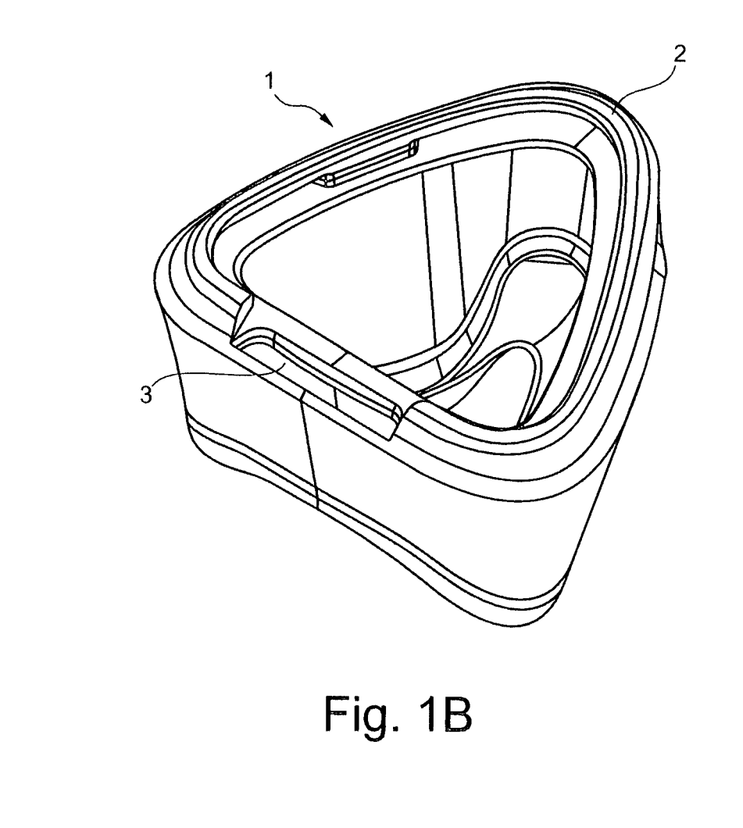
Figure 2A:
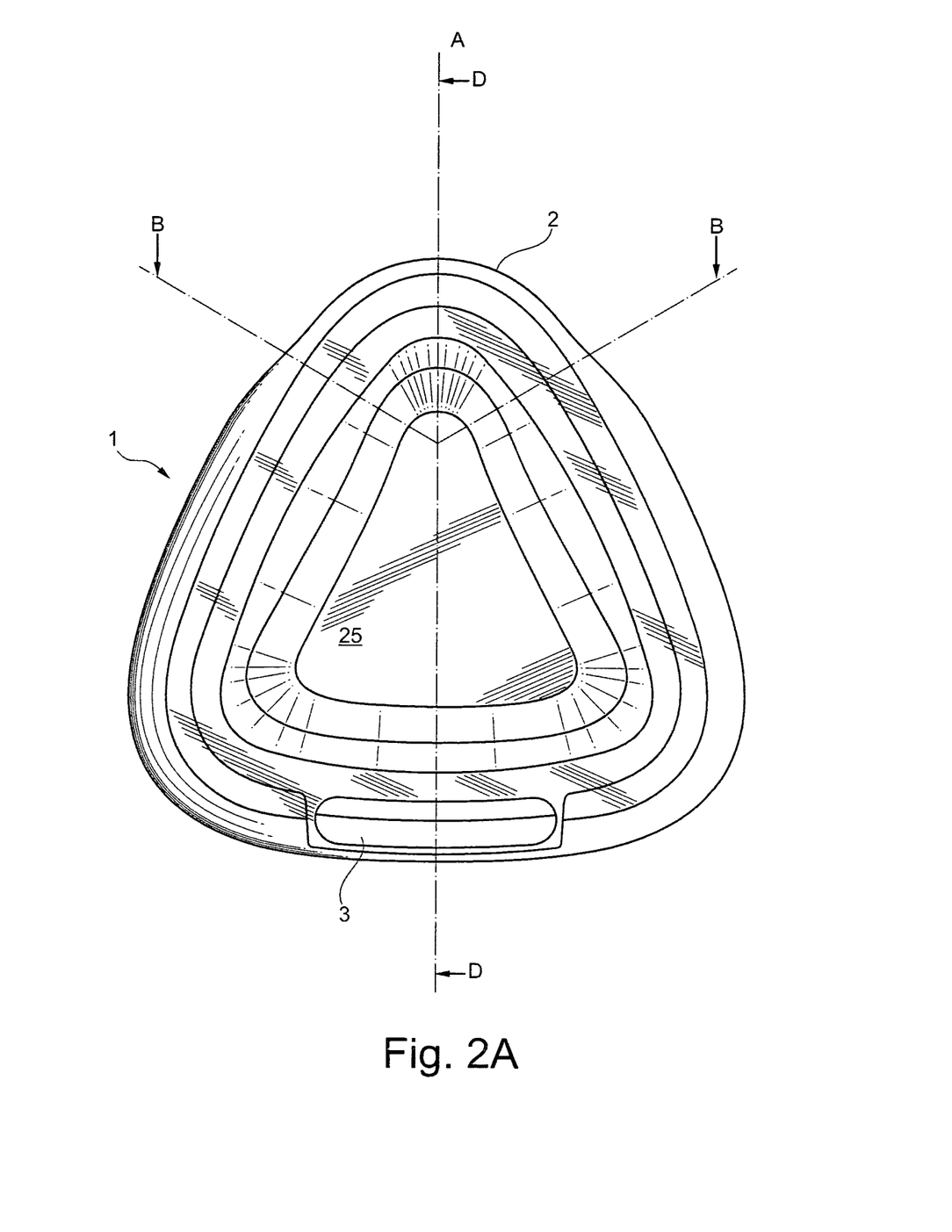
FIG. 2A (shaded) and FIG. 2B (line drawing) show a plan view of the cushion of FIG. 1.
Figure 2B:
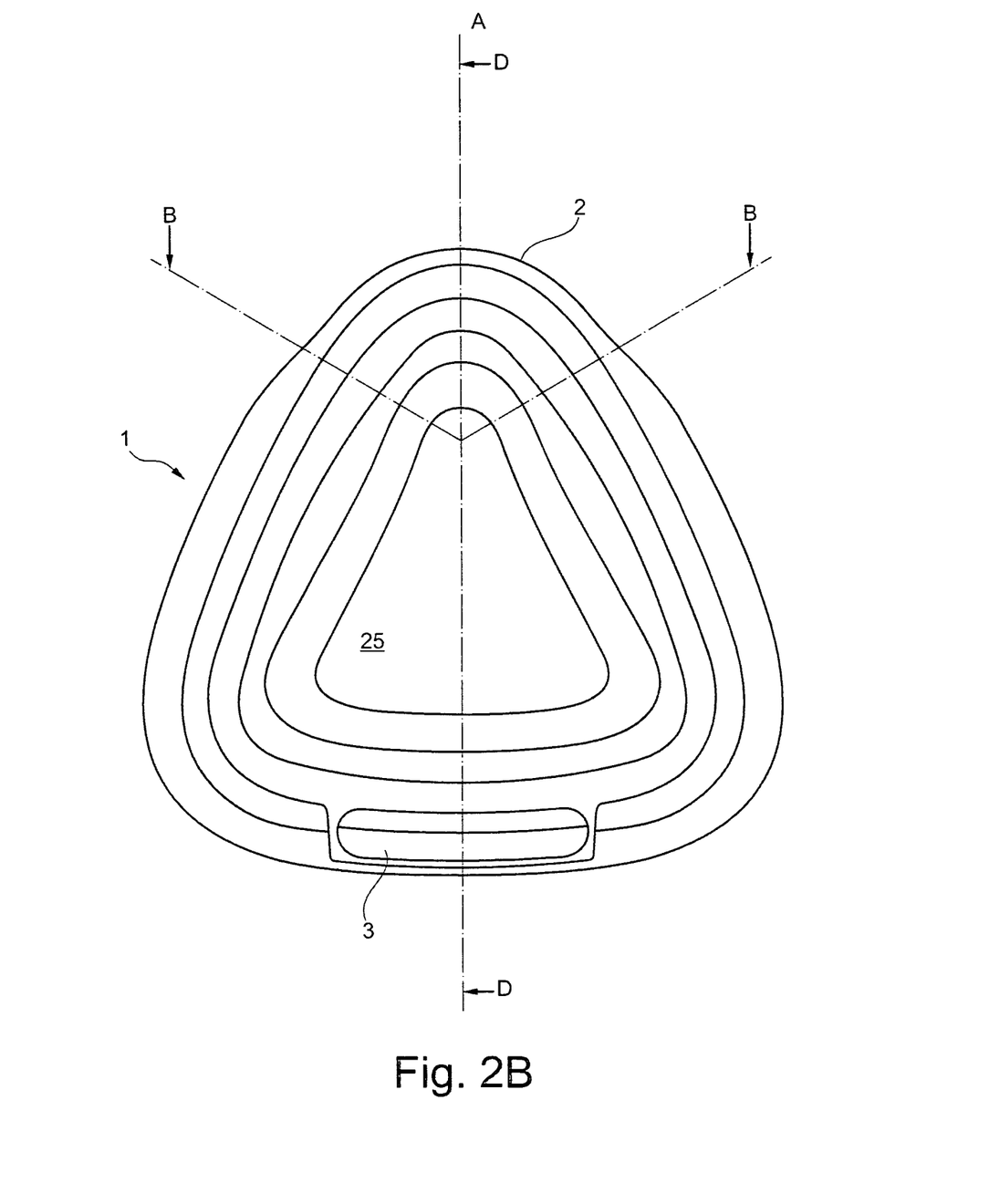

FIG. 1 (FIGS. 1A and 1B) show a perspective view of a preferred embodiment of a cushion 1 according to the present invention. The cushion 1 has a generally tube like circular or triangular shape with an opening 25 to receive a patient's nose and/or mouth. The tip 2 of the triangle is designed to be placed over the ridge of a patient's nose. At the base of the triangle, the cushion 1 comprises an orifice 3. This opening or orifice 3 is caused by the core used for creating a hollow cavity inside the cushion. The core was removed from the cushion after the molding process. In a later manufacturing step said orifice 3 may be closed, e.g. by injection-molding or gluing an insert into or a patch over the orifice. According to a further preferred method the orifice is closed by another injection molding step. Thus, a sealed cavity, which is not visible in FIG. 1, remains. FIG. 2 shows a plan view of the cushion of FIG. 1. FIGS. 1 and 2 show a view onto the cushion's side which is to be connected with a patient interface or face mask. Preferably, the exact one or at least one orifice 3 is not provided in the cushions side which is to contact a wearer's face. More preferably, orifice 3 is provided on the cushion's side to be connected to a patient interface, e.g. a mask shell or frame. This side may be opposite to the cushion's contact area, i.e., the area of the cushion to contact a wearer's face.

Of course, the general shape of the cushion 1 may deviate from the triangular shape shown in FIG. 1 and may be, e.g., round or oval or may have any other suitable shape. The shape of the cushion 1 is only constrained by its purpose, namely to fit to a patient's face. Preferably, the cushion fits over a patient's nose and/or mouth.

As can be seen in FIGS. 1 and 2, the orifice 3 is preferably arranged opposite to the cushions tip 2. Preferably, cushion 1 has mirror symmetry or is substantially mirror symmetric with regard to longitudinal axis A. Longitudinal axis A preferably runs through tip 2 of cushion 1. Orifice 3 is preferably also arranged symmetrically with regard to axis A.

The side of the cushion 3 to be connected to the patient interface such as a face mask or mask frame (not shown) is preferably adapted to be mechanically connected to such patient interface. Preferably, the cushion comprises connection means such as protrusions, depressions, hooks, grooves, undercuts, openings, pins and/or the like in order to allow such, preferably releasable, connection. The provision of integral fastening, handling and/or connection means allows the cushion to be secured to a breathing mask or a mask frame advantageously giving structural strength to the cushion by means of the mask frame. It furthermore allows easy replacement and exchangeability of an interface's cushion upon wear or contamination. Also, easy handling of the cushion, either during production or subsequently by the user, is achieved.

Figure 3A:
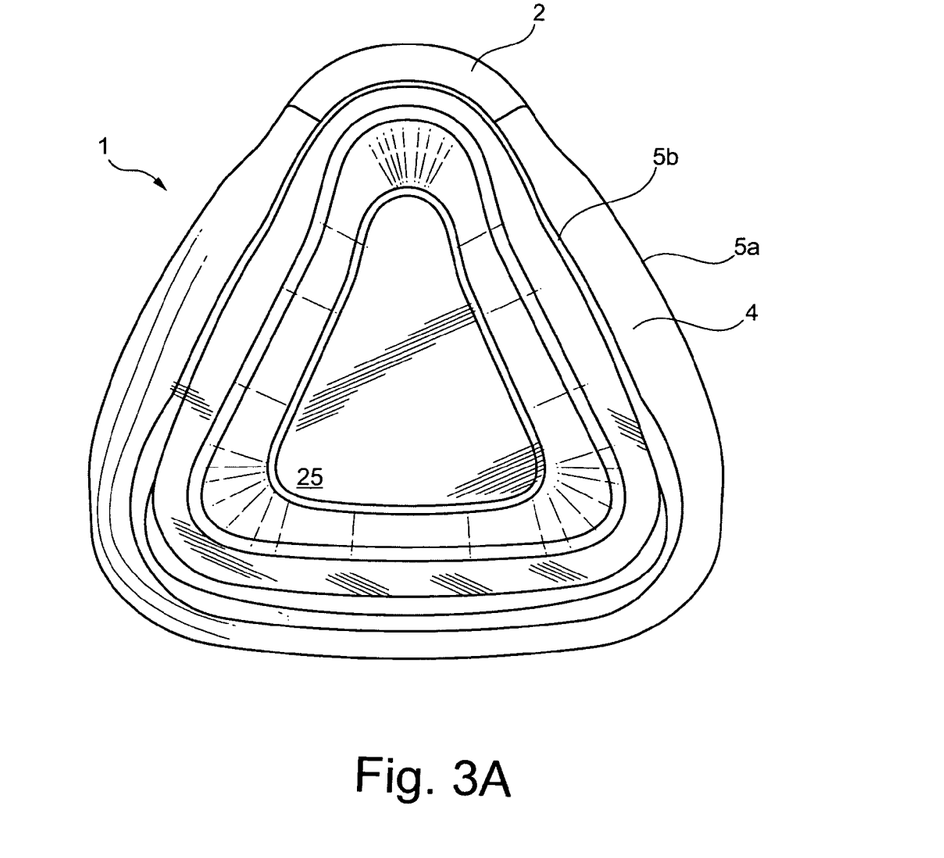
FIG. 3A (shaded) and FIG. 3B (line drawing) show a sectional view of the cushion of FIG. 1.
Figure 3B:
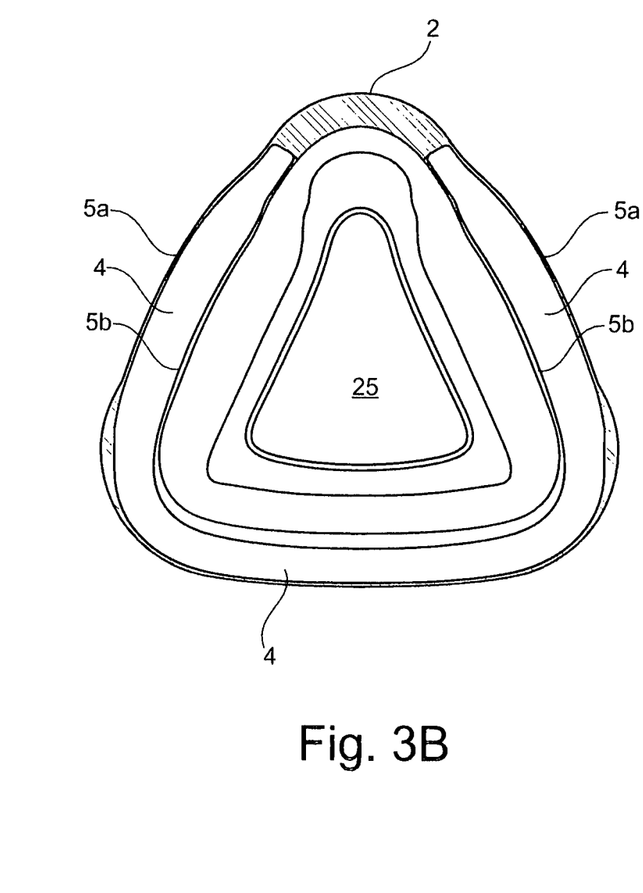
Figure 4A:
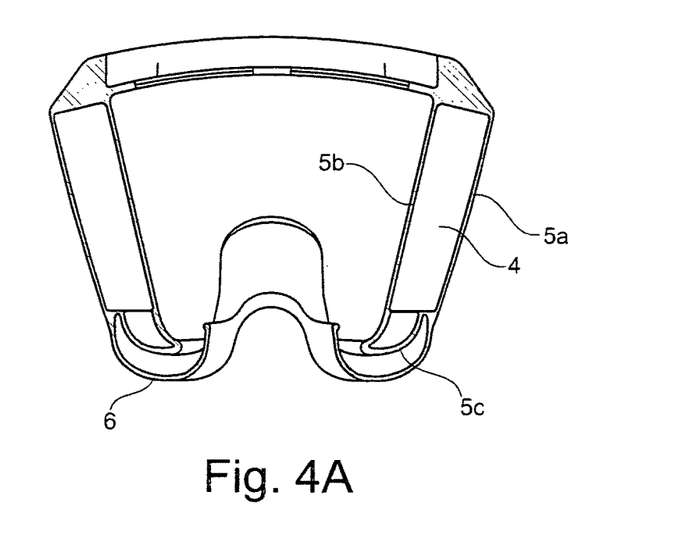
FIGS. 4A and 4B show another sectional view of the cushion of FIG. 1.
Figure 4B:
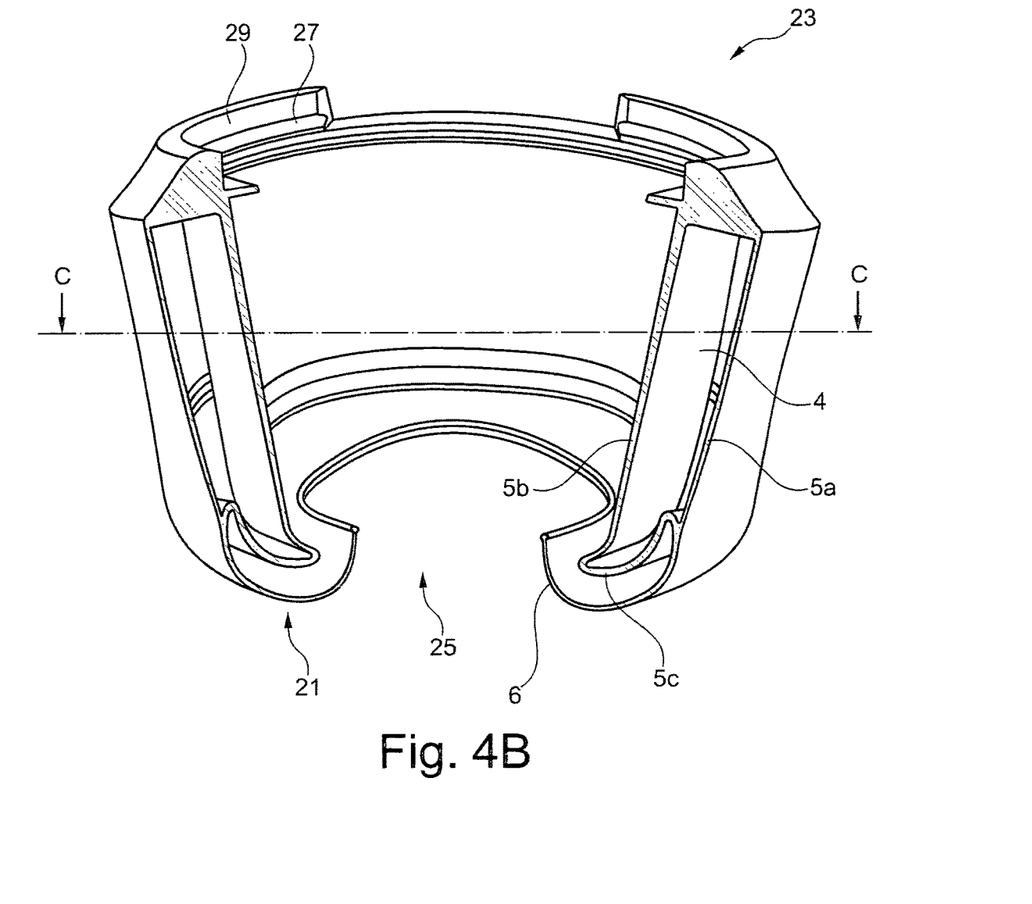

FIG. 3 shows a sectional view of the cushion of FIG. 1 about along the axis C-C shown in FIG. 4. In the sectional view of FIG. 3 the cavity 4 within the cushion 1 becomes visible. The cavity 4 extends along a portion of the circumference of the triangular cushion only: At the tip 2 of the triangle, i.e. proximate the patient's nose, the cavity is preferably omitted. Of course, the fraction of the circumference, in which the cavity is omitted may vary. The cavity 4 may, e.g., be much smaller (narrower and/or shallower) than the one shown in FIG. 3. For example, the cavity 4 may extend over one half, two third, three quarter or four fifth of the circumference of the cushion. As referred to above, the cushion is adapted to cover a wearer's nose and or mouth and is thus substantially ring shaped, e.g. triangular. It is however preferred that the cavity extends over most of the circumference, i.e. over 75 to 95%, most preferably over 80 to 90% of the circumference. According to a preferred embodiment, a cavity is only provided in defined regions along the cushions circumference or the cavity is only filled or filled with special filler in these regions. These regions preferably do not comprise the area contacting the patient's nose, the ridge of the nose, and/or the area of the patient's upper lip.

According to FIG. 3 the cavity has the shape of a slightly deformed "C". Depending on the overall shape of the cushion 1, the shape of the cavity 4 can vary accordingly.

In the embodiment shown there is provided one cavity extending over a substantial portion of the cushion's circumference. According to other preferred embodiments, there are provided two or more (horizontal) cavities which are separated by one or more horizontal walls or membranes. Horizontal is understood to be substantially parallel to the paper plane of FIG. 3 or substantially perpendicular to the paper plane of FIG. 4. In this case, there is preferably provided one core for each cavity. According to another or additional embodiment, the core comprises one or more slits which allow molding of the wall(s) or membrane(s) separating different cavities or pockets.

According to another preferred embodiment (not shown) there are provided two ore more (vertical) cavities or pockets which are separated by walls or membranes extending substantially vertically, i.e., perpendicular to the paper plane in FIG. 3 and substantially parallel to the paper plane in FIG. 4. In this case, there is preferably provided one core for each cavity. According to another or additional embodiment, the core comprises one or more slits which allow molding of the wall(s) or membrane(s) separating different cavities or pockets. Preferably, the cushion comprises both one or more horizontal cavities and one or more vertical cavities.

The cushion 1 comprises preferably silicone, TPE and/or oil. The cushion can in particular be manufactured by injection-molding silicone into a mold. It is further preferred that the cavity 4 is filled with a second material. Preferred examples for the second material are foams, gels, liquids and gases. Preferably, the second material is a silicone gel or other material discussed herein. It is particularly preferred that the second material has a lower Shore-hardness than the first material. Preferably, the Shore hardness of the second material lies in the range referred to above. Preferably, the shore hardness of the first material varies as discussed above. More preferred, the relation of the Shore hardness of the first and second material is such as discussed above. If the cushion comprises more than one cavity, these cavities are preferably filled with second material of different Shore hardness. Preferably, one cavity is filled with second material(s) of different Shore hardness. For example, the cavity may be filled with different layers of second material, wherein each layer exhibits a different Shore hardness. Preferably, such layers are horizontal layers (approximately parallel to the paper plane of FIG. 3).

It should be apparent from FIG. 3, that the general hardness or rigidity of the cushion 1 largely depends on the characteristics of the second material(s) filled into the cavity 4. However, it also depends on the properties of the walls 5a, 5b of the cavity, i.e. the cushion frame. It is thus possible to also control the rigidity of the cushion by varying the thickness of the cushion walls 5a, 5b. According to the inventive method this can be achieved by varying the thickness of the core: A core of increased thickness used in combination with the same mold halves will lead to thinner walls 5a, 5b, while a thinner core will result in thicker walls 5a, 5b. Alternatively or additionally, the rigidity of the cushion can be adjusted by providing ribs and/or grooves within the inner surface of the cushion, i.e. on the surfaces of the wall 5a, 5b facing inside the cavity 4. Therein, providing ribs and/or grooves is preferably achieved by providing corresponding grooves and/or ribs on the surface of the core.

Thus, the properties of the cushion, in particular its flexibility, hardness and elasticity, can be easily adjusted by varying the thickness of the cavity walls 5a, 5b, by varying the number and extension of cavities (horizontal, vertical), and/or by varying the properties of the second material(s) inside the cavity/cavities. This allows a fine and exact adjustment of the cushion properties in line with the object underlying the present invention.

Moreover, the geometry of the cushion walls as well as of the cavity can be achieved by providing a different core while using one and the same mold halves. Thus, the outer geometry of the cushion remains identical wherein is inner geometry or structure is changed, thereby adjusting the cushions overall properties. This largely simplifies the process of manufacturing different cushions adapted for specific applications and thus reduces the production costs per unit. This also allows the provision of a unified fastening structure to connect cushions with different properties, such as sizes and hardness distribution, to patent interfaces.

FIG. 4 shows another sectional view of the cushion of FIG. 1, taken along line B-B in FIG. 2. 4 shows a first (or lower regarding the orientation shown in FIG. 4) cushion portion 21 which is to sealingly and comfortably contact a user's face. This portion is also referred to as the cushion's contact portion or contact side. Preferably, such contact portion 21 comprises a sealing lip 6 for enhancing the sealing properties of the mask. Such lip 6 also positively influences the wearing comfort of the cushion and its patient interface. Preferably, sealing lip 6 extends from the cushion's outer wall 5a along the contact portion 21 towards the inner wall 5b of the cushion 1. When the cushion is not contacting a patient, lip 6 is preferably distanced from the cushion's lower wall 5c. In use, lip 6 contacts a user's face.

Cushion 1 furthermore comprises a second (or upper regarding the orientation shown in FIG. 4) cushion portion or side 23. This side is for being connected to a patient interface (not shown) such as a face mask. Connection side 23 preferably comprises fastening means as referred to above (see rim 29 and groove 27) for connection or fastening the cushion 1 to/with a patient interface body or frame.

Figure 5A:
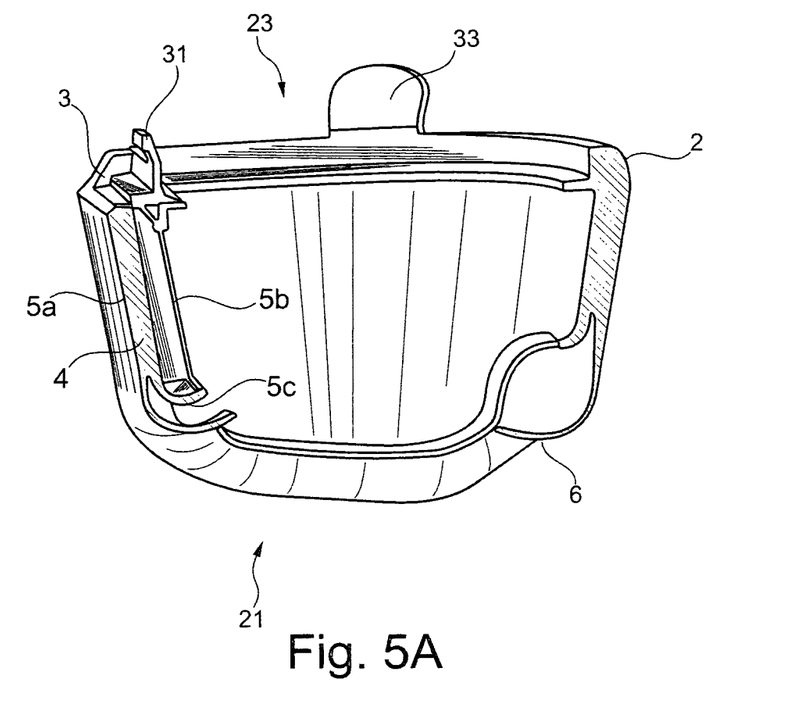
FIG. 5A (shaded) and FIG. 5B (line drawing) show another sectional view of the cushion of FIG. 1.
Figures 5B, 5C:
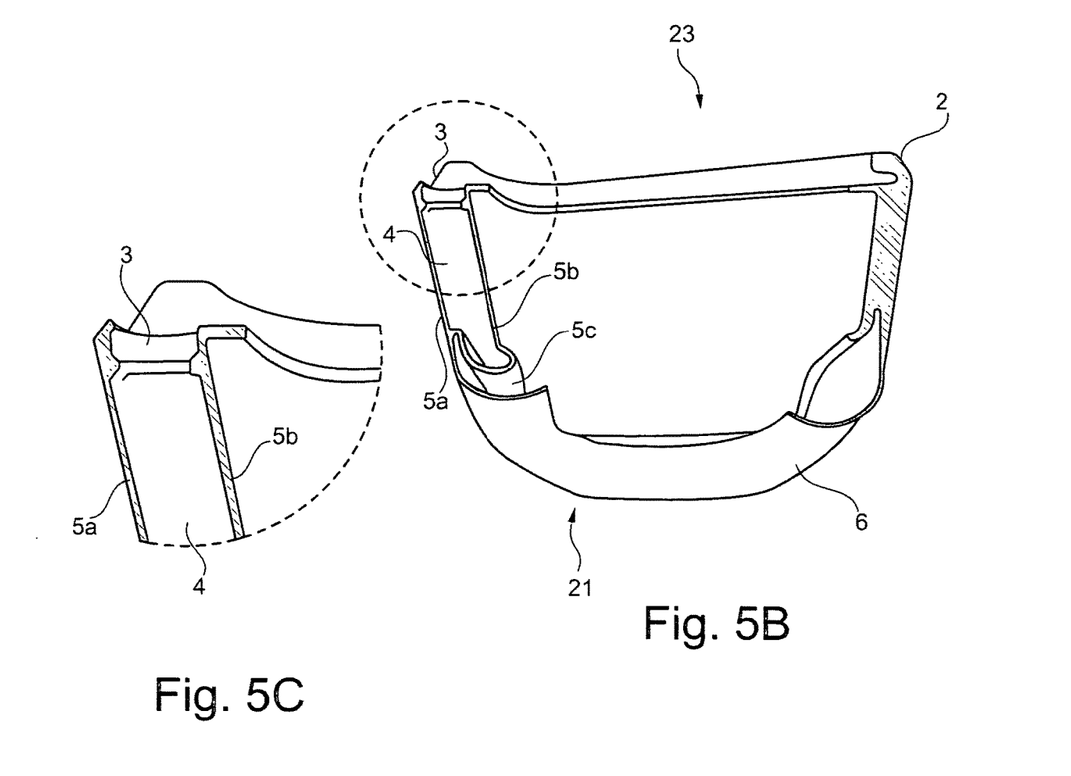

FIG. 5 shows another sectional view of the cushion of FIG. 1 taken along line D-D through the tip 2 of the cushion. Since the cavity 4 does not extend along the whole circumference of the cushion 1, omitting in particular the region proximate the patient's nose, in FIG. 5 the cavity 4 is visible in the left part of the cushion only. FIG. 5 also shows the orifice 3 through which the core extends when cushion 1 is molded and which is preferably used for filling the cavity with second material(s). Preferably, cushion 1 is molded with handling means 33 provided at the exterior for improved handling, during use or production. Such handling means can also be, as discussed above, be applied as a lid for orifice 3. Furthermore, cushion 1 is preferably provided with some fastening means 31 or lid means in the area of orifice 3 for improving closing and sealing of orifice 3 and/or for providing a securing means for a cushion 3 to, e.g., a mask frame.

Figure 6:
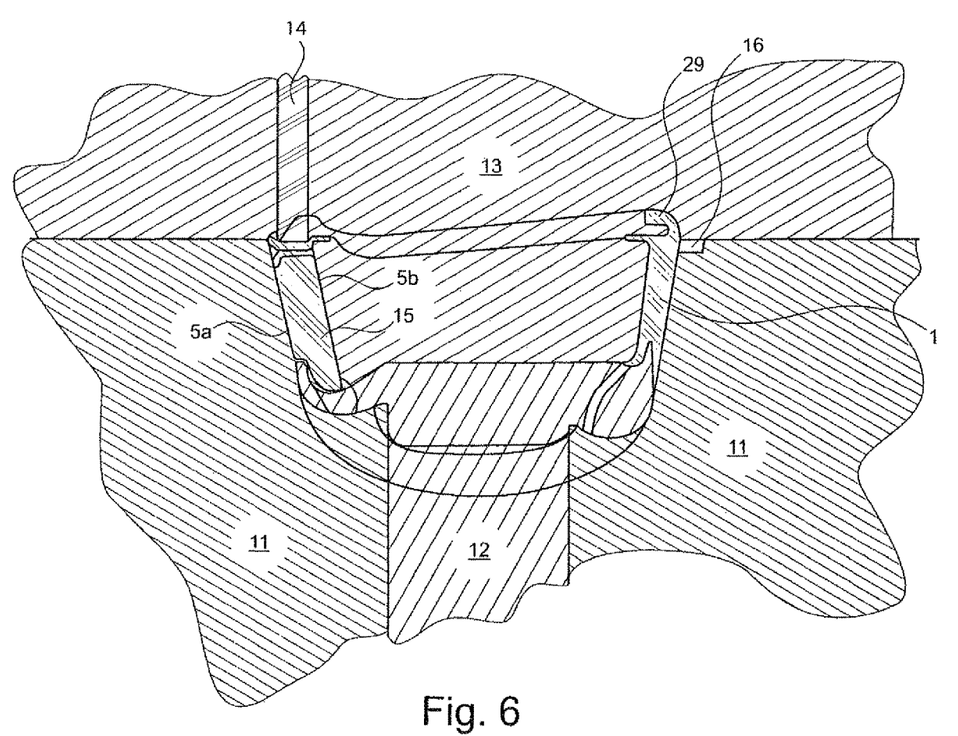
FIG. 6 schematically illustrates the method of manufacturing according to the present invention.

FIG. 6 schematically illustrates the method of manufacturing as well as a preferred apparatus for manufacturing according to preferred embodiments of the present invention. According to such embodiment, three mold parts 11, 12 and 13 are provided. They are moveable with respect to each other. Thus, the mold can be opened and closed. Mold half 13 is designed complementary to the cushion's upper side 23 and to its inner side such as inner wall 5b. Mold half 11 is designed complementary to the cushion's outer circumference and part of the cushion's lower side 21. Stamp 12 is designed complementary to the remainder of the cushion's lower side 21 and is adapted to form sealing lip 6.

Furthermore, a core 15 is provided within the mold formed by said mold parts 11, 12 and 13. The core is preferably C-shaped and mounted on or comprises a handling member 14 such as, e.g., a rod. Preferably, core 15 is substantially symmetrical with regard to axis A of the cushion to be molded, as shown, e.g., in FIG. 2. Preferably, core 15 and member 14 are integrally formed. Preferably, member 14 is moveably connected to mold half 13. Core 15 can thus be displaced with respect to the mold parts 11, 12 and 13.

After closing the mold, a first material is injected into the mold through gate 16. The first material is cured or at least partially cured and thus a cushion 1 is formed. The core 15 is enclosed by the cushion 1 and thus forms a cavity 4 therein. Handling member 14 extends through orifice 3 to the outside of cushion 1. The mold is then opened by moving, e.g., mold parts 11 and 12 away from mold part 13. The moveable part 14 is then displaced with respect to mold part 13, preferably leaving the core 15 together with the cushion 1 in a position without any contact to other mold parts. Now, the cushion 1 may be removed from the core 15. This may be achieved, e.g. by air pressure. For instance, member 14 and core 15 may comprises an air conduit for providing pressure. The cavity of the cushion 1 formed by the core 15 is thus inflated and the cushion 1 can be easily detached from the core 15. Alternatively, cushion 1 can be mechanically pulled of the core 15 without the provision of air pressure.

Of course, the mold parts can be designed differently. According to a preferred embodiment only two mold parts 11, 13 are provided instead of the three mold parts 11, 12 and 13. According to another preferred embodiment, it is also preferred to provide one or more additional pin(s), which are moveable with respect to mold part 13 in a manner comparable to member 14. Thus, the cushion 1 is better supported when displacing the core 15 with cushion 1 from the mold part 13 and an unnecessary stretching or deforming of the cushion 1 is avoided. These pins preferably also serve to support the proper positioning of core 15. After molding, there will be a small hole, preferably with a diameter of a few milimeters, in the cushion where the pin has been. These hole(s) will be sealed in the sealing step for sealing orifice 3. Preferably, the hole(s) left by the pin(s) a advantageous, such as orifice 3, in that they allow air to escape from the cavity during filling thereof.

Demolding of the cushion 1 from the core 15 is possible due to the large degree of elastic expansion that the first material, such as silicone or polysiloxane, provides. Elongation or elasticity of the first material preferably lies in the range of about 300% to 400% after molding when the material is still warm. However, other comparable materials having a sufficiently large degree of elastic expansion can be used instead.

Preferably, the preferably C-shaped core is of large dimensions while the hole is of small, preferably substantially rectangular, dimension. The ratio between the maximum width (referring to a top view and orientation according to e.g. FIG. 1) of the core and the respective width of the orifice lies preferably in the range between 1/1.2 and 1/2.5 and is preferably about 1/2. Alternatively or in addition, the ratio between the maximum height of the core (referring to a side view and orientation according to e.g. FIG. 4) and the respective length of the orifice (referring to a top view and orientation according to e.g. FIG. 1) lies preferably in the range between 1/4 to 1/8 and is preferably about 1/6. While the above dimensions and ratios preferably apply to the core, cavity and opening of a nasal cushion it will be well understood to adapt the respective measures to apply to, e.g., a full face cushion covering both, nose and mouth. Preferably, for such core and/or orifice, the dimensions in the width direction increase by a factor of about 1.1 to 1.4 and preferably of about 1.2 to 1.3, the dimensions in the length direction increase by a factor of about 1.5 to 1.8 and preferably of about 1.6 to 1.7, and/or the dimension in the height direction preferably increase by a factor of about. 1 to 1.4, preferably of about 1.1 to 1.2. Reference to dimension made herein generally refers to the directions as mentioned in brackets above.

According to a preferred embodiment, as discussed above, if multiple horizontal and/or vertical cavities or pockets are to be provided in cushion 1, multiple cores or core parts are connected to handling member 14. In such embodiment, handling member 14 preferably extends into an atrium of cavity 4 which is adjacent orifice 3. From said atrium there extend cores or core parts to form the different cavities or different parts of the cavity. Also with this embodiment, there is preferably provided only one core per cavity.

Orifice 3 is preferably adapted to allow handling member 14 to extend therethrough and also to allow the core(s) to be withdrawn therethrough during demolding. Preferably, orifice 3 is about 20 to 30, preferably to 50 mm, preferably 30 to 50 mm, and more preferably about 35 to 40 mm wide and about 3 to 10 mm long. The shape and dimensions of orifice 3 correspond to the cross section of member 14 of core 15 extending therethrough during molding. Orifice 3 is preferably arranged on fastening side 23 of the cushion to be molded.

Removing the core 15 from the cushion 1 leaves a cavity 4 within the cushion and at least one orifice 3, where the core 15 was connected to the member 14. Said orifice 3 is closed in a later production step in order to seal the cavity 4. Preferably, the cavity 4 is filled with a second material, such as a silicone gel or foam, before the sealing step. As discussed above, different cavities are preferably filled with different second materials but may also be filled with the same material having the same properties. According to a preferred embodiment, the cavity is filled with different second materials, e.g. in horizontal layers. Such different second materials can be the same basic material but having different hardness and elasticity properties.

According to a further preferred embodiment, the cushion 1 is molded as discussed above. After molding the mold is opened, e.g., by removing mold half 13. Then, the core is removed from the cavity/cavities via orifice 3. In such case, orifice 3 may extend over the whole length of the cavity along the cushion's circumference. In a next step, at least one second material is filled into the cavity/cavities. Subsequently, preferably after the mold halves have been closed again, orifice 3 is closed by injecting a second shot of the first material. By such second injection the cavity is sealed. Preferably, some outer structures of the mask are provided, e.g., as fastening means such as rim 29 and/or groove 27. Said groove 27 may be adapted as a handling member, e.g., to be used in an automatic demolding step. For example, a robot may grip the cushion making use of said groove 27 in order to detach the cushion from the core.

As referred to above, core 15 can be provided with structures such as grooves, slits, rims, depressions, allowing to influence both the geometry of the cavity and the geometry of the cushion walls. Thereby, and particularly in combination with a specific choice of the properties of first and/or second material, the cushion properties can be advantageously influenced and adjusted. In particular, the invention allows such adjustment without changing the outer dimensions of the cushion and particularly its fastening portion. Thus, the patient interface to which the cushion has to be secured and its fastening structure can remain unchanged. The same applies to the mold parts 11, 12, 13 forming the outer dimension of the cushion. These do not have to be changed or replaced together with the core.

The method according to the present invention is advantageous over the prior art since it, i.a., allows for an easy and well-controlled production of cushions for respiratory masks. In particular, the method can be easily automated. One reason for this is the fact that a single core is used, which can be easily placed within the mold correctly and simply removed from the cushion after curing. Preferably, even the demolding of the core can be automated. During molding and demolding the core is maintained inside the mold and connected to one of the mold halves. Thus, the temperature of the core can be better maintained and controlled, which is important in terms of reproducibility.

A further advantage of the inventive method is the cost-efficient control the rigidity, resilience and flexibility of the cushion by, e.g., varying the thickness of the cushion walls and the dimension of the cavity. As can be taken from FIG. 6 a core 15 of increased thickness used in combination with the same mold parts 11, 12 and 13 will lead to thinner walls 5a, 5b, while a thinner core 15 will result in thicker walls 5a, 5b. The same applies to the core's extensions in the vertical direction of FIG. 6. Alternatively or additionally, the rigidity of the cushion 17 can be adjusted by providing ribs and/or grooves within the inner surface of the cushion, i.e. on the surfaces of the wall 5a, 5b facing inside the cavity. Therein, providing ribs and/or grooves is preferably achieved by providing grooves and/or ribs on the surface of the core 15.

Thus, the properties of the cushion, in particular its flexibility and elasticity, can be easily adjusted by providing different cores while using one and the same mold parts and leaving the remainder geometry of the cushion unchanged. This largely simplifies the process of manufacturing different cushions adapted for specific applications and thus reduces the production costs per unit. Manufacturing of the cushion can thus be automated. Alone the core of the mold allows beneficial manufacturing of an adjusted and improved cushion. The integral nature of the core, particularly in combination with the handling member, allows omitting manual intervention of handling, allows predefined and repeatable position of the core, and the core to substantially maintain a temperature equilibrium with the mold while the mold is opened. The present invention thus provides for an improved, efficient, effective and reliable method for molding cushions, a cushion and a device for molding cushions.

The invention claimed is:

1. A method of manufacturing a cushion for a respiratory mask, comprising:
   providing a mold, the mold comprising at least two mold halves and at least one core, the at least one core being C-shaped;
   closing the mold around the core;
   injecting a first material into the mold and around the at least one core to enclose the core by the first material and form the cushion as a one-component structure with a central through hole;

opening the mold; and
removing the core from within the cushion through a single orifice; and
sealing the orifice after the core is removed from within the cushion;
wherein:
removal of the core from within the cushion creates at least one cavity completely surrounded by the cushion but for the single orifice through which the core is removed;
a cross section along a central axis of the central through hole immediately after removal of the core includes an uninterrupted perimeter around the at least one cavity;
the single orifice provides the only fluid communication between the at least one cavity and an environment external to the cushion; and
the at least one cavity is defined solely by the first material of the surrounding cushion.

2. The method according to claim 1, wherein removing the core from the cushion comprises displacing the core together with the cushion relative to the mold halves.

3. The method according to claim 1, further comprising sealing the cavity by one or more of injecting the first material into the orifice, gluing an insert into the orifice, gluing a patch over the orifice, and overmolding the cushion including the orifice.

4. The method according to claim 1, further comprising filling the cavity with a second material prior to sealing the cavity.

5. The method according to claim 4, wherein the second material comprises at least one foam, gel, liquid, gas, or beads, or a combination thereof.

6. The method of claim 4, wherein the second material is silicone.

7. The method according to claim 1, further comprising adjusting rigidity of the cushion by varying thickness and/or structure of a cushion wall along a cross section and/or circumference of the cushion wall.

8. The method according to claim 1, further comprising adjusting rigidity of the cushion by providing ribs and/or grooves on an inner surface of the cushion or within the inner surface of the cushion, the inner surface of the cushion comprising inner cavity walls.

9. The method according to claim 1, further comprising creating the cushion with varying thickness by varying a thickness of the core.

10. The method according to claim 9, further comprising creating protruding structures on the cushion.

11. The method according to claim 10, wherein the protruding structures are created by providing complementary structures on a surface of the core.

12. The method according to claim 11, wherein the complementary structures are grooves and/or ribs.

13. The method according to claim 1, further comprising creating two or more horizontal or longitudinal cavities which are separated by one or more horizontal walls or membranes.

14. The method according to claim 13, further comprising forming two or more vertical or transverse cavities or pockets which are separated by walls or membranes extending substantially vertically.

15. The method of manufacturing a cushion for a respiratory mask according to claim 1, further comprising:
stretching the cushion to allow the core to be removed from the cushion through the orifice; and
returning the cushion to a predetermined molded shape after the core is removed from the cushion.

16. The method according to claim 1, further comprising forming two or more vertical or transverse cavities or pockets which are separated by walls or membranes extending substantially vertically.

17. A method for manufacturing a cushion usable in a respiratory mask, the method comprising:
injecting a first elastomeric material into a mold, the mold comprising at least two mold segments and at least one core enclosed within a chamber defined by the mold segments, to form a one-component cushion body within the mold, the cushion body forming around and substantially enclosing the at least one core, the cushion body having at least one substantially enclosed cavity formed by the core and an opening sized to fit around a patient's nose, the at least one cavity being substantially surrounded by the first material so that a cross section of the one-component cushion body along a central axis of the opening includes an uninterrupted perimeter of the first elastomeric material around the at least one cavity prior to removal of the at least one core from the cushion body; and
removing the cushion body from the at least one core such that only a single orifice through which the cushion body was removed provides fluid communication between the at least one cavity and an environment external to the cushion body.

18. The method according to claim 17, further comprising sealing the cavity.

19. The method according to claim 18, further comprising: filling the at least one cavity with a second material prior to sealing the cavity.

20. The method according to claim 17, further comprising forming the orifice to be continuous with the cushion body, deformable, and around a portion of the core.

21. The method according to claim 20, wherein a width of the orifice is approximately half a maximum width of the core.

22. The method according to claim 20, wherein a length of the orifice is between approximately one-fourth and one-eighth a maximum height of the core.

23. The method according to claim 20, further comprising attaching the at least one core to a handling member that is moveable with respect to at least one of the mold segments.

24. The method according to claim 23, further comprising placing the handling member to extent through the orifice during and withdrawing the at least one core from the cushion body through the orifice during demolding using the handling member.

25. The method according to claim 17, further comprising:
creating protrusions and/or indentations on inner surfaces of walls bounding the at least one cavity with the core; and
locating the protrusions and/or indentations to locally vary a rigidity of the cushion body.

26. The method according to claim 17, further comprising:
creating variations in thickness in the cushion with variations in thickness of the core.

27. The method of manufacturing a cushion for a respiratory mask according to claim 17, further comprising:
stretching the cushion body to allow the core to be removed from the cushion body through the orifice; and
returning the cushion body to a predetermined molded shape after the core is removed from the cushion body.

28. A cushion usable in a respiratory mask, comprising:
a cushion body formed from a first elastomeric material around a central through hole; and
at least one enclosed cavity inside the cushion body, wherein a cross section along a central axis of the central through hole includes an uninterrupted and continuous perimeter of the first elastomeric material around the cavity;
wherein only a single fillable orifice provides fluid communication between the at least one enclosed cavity and an environment external to the cushion body.

29. The cushion according to claim 28, wherein the cushion comprises two or more horizontal or longitudinal cavities which are separated by one or more horizontal walls or membranes.

30. The cushion according to claim 29, and wherein the cushion also comprises two or more vertical or transverse cavities or pockets which are separated by walls or membranes extending substantially vertically.

31. The cushion according to claim 28, wherein a ratio between a width of the orifice and a width of the cavity is in the range from about 1/1.5 to 1/2.5, and/or wherein the ratio between a length of the orifice and a height of the cavity lies in a range from about 1/5 to 1/7.

32. The cushion according to claim 31, wherein the ratio between the width of the cavity and the width of the orifice is about 1/2.

33. The cushion according to claim 31, wherein the ratio between the length of the orifice and the height of the cavity is about 1/6.

34. The cushion according to claim 28, wherein the cushion comprises only one of the enclosed cavity and the enclosed cavity is a C-shaped cavity extending only along a part of a circumference of the cushion.

35. The cushion according to claim 28, wherein the orifice is deformable.

36. The cushion according to claim 28, wherein:
the cushion body has protrusions and/or indentations on at least one inner wall bounding the at least one cavity; and
the protrusions and/or indentations locally vary a rigidity of the cushion body.

37. The cushion according to claim 28, wherein:
the cushion body has varying thickness to vary rigidity of the cushion body at different locations.

38. The cushion for a respiratory mask according to claim 28,
wherein:
the cushion body is configured to stretch at least in a region containing the orifice; and
the cushion body is configured to resiliently return to a predetermined molded shape after the region containing the orifice is stretched.

39. The cushion according to claim 28, wherein the cushion comprises at least one C-shaped cavity extending only along a part of a circumference of the cushion.

40. The cushion according to claim 28, wherein the cushion comprises two or more vertical or transverse cavities or pockets which are separated by walls or membranes extending substantially vertically.

41. A cushion for a respiratory mask comprising:
a cushion body comprising a first material, the cushion body including a central through hole that is sized to fit over and around a patient's nose; and
an enclosed cavity within the cushion body;
wherein:
the cushion body is a continuous, hollow structure but for a single orifice;
a cross section of the cushion body along a central axis of the central through hole comprises an uninterrupted perimeter of the first material around the enclosed cavity; and
the enclosed cavity is substantially C-shaped.

* * * * *